US011939561B2

(12) United States Patent
Kronenberg

(10) Patent No.: US 11,939,561 B2
(45) Date of Patent: Mar. 26, 2024

(54) PROCESS FOR ASSEMBLING PACKAGING FOR A FLEXIBLE CONTAINER

(71) Applicant: Sartorius Stedim Biotech GmbH, Goettingen (DE)

(72) Inventor: Diana Kronenberg, Berlin (DE)

(73) Assignee: SARTORIUS STEDIM BIOTECH GMBH (DE)

( * ) Notice: Subject to any disclaimer, the term of this patent is extended or adjusted under 35 U.S.C. 154(b) by 1323 days.

(21) Appl. No.: 16/438,815

(22) Filed: Jun. 12, 2019

(65) Prior Publication Data

US 2019/0292506 A1 Sep. 26, 2019

Related U.S. Application Data

(62) Division of application No. 15/112,337, filed as application No. PCT/EP2014/076494 on Dec. 4, 2014, now abandoned.

(30) Foreign Application Priority Data

Feb. 13, 2014 (DE) .................. 10 2014 101 839.7

(51) Int. Cl.
- *B65B 5/04* (2006.01)
- *B01F 27/072* (2022.01)

(Continued)

(52) U.S. Cl.
CPC ......... *C12M 23/26* (2013.01); *B01F 27/0723* (2022.01); *B01F 27/0724* (2022.01);

(Continued)

(58) Field of Classification Search
CPC ........... B65B 5/04; B65B 25/00; B65B 43/00; B65D 19/385; B65D 88/20; B65D 90/20;

(Continued)

(56) References Cited

U.S. PATENT DOCUMENTS

| 2,936,984 A | * | 5/1960 | Skubic | ................ | B65D 19/385 |
| | | | | | 108/53.5 |
| 3,372,725 A | * | 3/1968 | Voorhees | ............... | B65D 88/20 |
| | | | | | 222/105 |

(Continued)

FOREIGN PATENT DOCUMENTS

| CN | 1274385 A | 11/2000 |
| CN | 101356261 A | 1/2009 |

(Continued)

OTHER PUBLICATIONS

PCT International Search Report and Written Opinion dated Jun. 30, 2015 from corresponding Application No. PCT/EP2014/076494, 17 pages.

(Continued)

*Primary Examiner* — Stephen F. Gerrity
(74) *Attorney, Agent, or Firm* — Dilworth IP, LLC

(57) ABSTRACT

A packaging for a flexible container, in particular for a disposable bag for use in a bioreactor, including a bottom part for fixing a first portion of the container, a ceiling part for fixing an opposite second portion of the container, a receiving space which on a first side is defined by the bottom part and on an opposite second side is defined by the ceiling part, and struts arranged between the bottom part and the ceiling part, which fix a defined distance between the bottom part and the ceiling part.

4 Claims, 3 Drawing Sheets

(51) Int. Cl.
| | |
|---|---|
| *B01F 27/191* | (2022.01) |
| *B01F 27/88* | (2022.01) |
| *B01F 27/91* | (2022.01) |
| *B01F 33/453* | (2022.01) |
| *B01F 35/513* | (2022.01) |
| *B65B 25/00* | (2006.01) |
| *B65D 6/24* | (2006.01) |
| *B65D 19/38* | (2006.01) |
| *B65D 19/40* | (2006.01) |
| *B65D 77/00* | (2006.01) |
| *B65D 77/04* | (2006.01) |
| *C12M 1/00* | (2006.01) |
| *C12M 1/12* | (2006.01) |
| *B01F 101/44* | (2022.01) |

(52) U.S. Cl.
CPC ............ *B01F 27/191* (2022.01); *B01F 27/88* (2022.01); *B01F 27/91* (2022.01); *B01F 33/4531* (2022.01); *B01F 35/513* (2022.01); *B65B 5/04* (2013.01); *B65B 25/00* (2013.01); *B65D 11/1873* (2013.01); *B65D 19/385* (2013.01); *B65D 19/40* (2013.01); *B65D 77/003* (2013.01); *B65D 77/0466* (2013.01); *C12M 23/14* (2013.01); *C12M 23/28* (2013.01); *C12M 25/06* (2013.01); *B01F 2101/44* (2022.01); *B65D 2519/00532* (2013.01)

(58) Field of Classification Search
CPC ...... B65D 2519/00532; B65D 2585/64; B65D 2585/641; B65D 2585/649; B65D 2585/6897
USPC ............................................ 53/452; 206/319
See application file for complete search history.

(56) References Cited

U.S. PATENT DOCUMENTS

| | | | |
|---|---|---|---|
| 3,556,886 A | 1/1971 | Reusser | |
| 4,036,361 A * | 7/1977 | Jacobson et al. | B65D 88/20 220/6 |
| 4,290,300 A | 9/1981 | Carver | |
| 5,307,928 A | 5/1994 | Bishop | |
| 5,622,277 A * | 4/1997 | Van Giezen et al. | B65D 90/205 220/9.4 |
| 5,897,012 A | 4/1999 | Sortwell | |
| 6,029,839 A | 2/2000 | Mansouri | |
| 6,463,863 B1 * | 10/2002 | Ishikawa et al. | B65D 19/385 108/55.1 |
| 7,713,734 B2 | 5/2010 | Ghosh et al. | |
| 2005/0045639 A1* | 3/2005 | Thorpe | B65D 19/385 220/495.01 |
| 2005/0269229 A1* | 12/2005 | Lowry | B65D 19/385 211/74 |
| 2005/0272146 A1 | 12/2005 | Hodge et al. | |
| 2009/0219780 A1* | 9/2009 | Castillo et al. | C12M 27/02 366/132 |
| 2009/0260551 A1 | 10/2009 | Mattson | |
| 2011/0310696 A1 | 12/2011 | Goodwin et al. | |
| 2012/0241447 A1 | 9/2012 | Starnes | |
| 2016/0040109 A1 | 2/2016 | Dahlberg et al. | |
| 2016/0114935 A1* | 4/2016 | Rönnholm et al. | C12M 27/02 220/601 |

FOREIGN PATENT DOCUMENTS

| | | |
|---|---|---|
| DE | 10215023 A1 | 10/2003 |
| DE | 202012005989 U1 | 7/2012 |
| DE | 102012204540 A1 | 9/2012 |
| EP | 1462155 A1 | 9/2004 |
| GB | 2189773 A | 11/1987 |
| WO | 2010074953 A1 | 7/2010 |
| WO | 2013171340 A2 | 11/2013 |

OTHER PUBLICATIONS

PCT International Preliminary Report on Patentability dated Aug. 16, 2016 from corresponding Application No. PCT/EP2014/076494, 14 pages.
German Office Action dated Sep. 4, 2014 from corresponding DE Application No. 10 2014 101 839.7, along with English summary.
Chinese Office Action dated Jul. 31, 2017 from corresponding CN Patent Application No. 201480075247.8, along with English summary.

\* cited by examiner

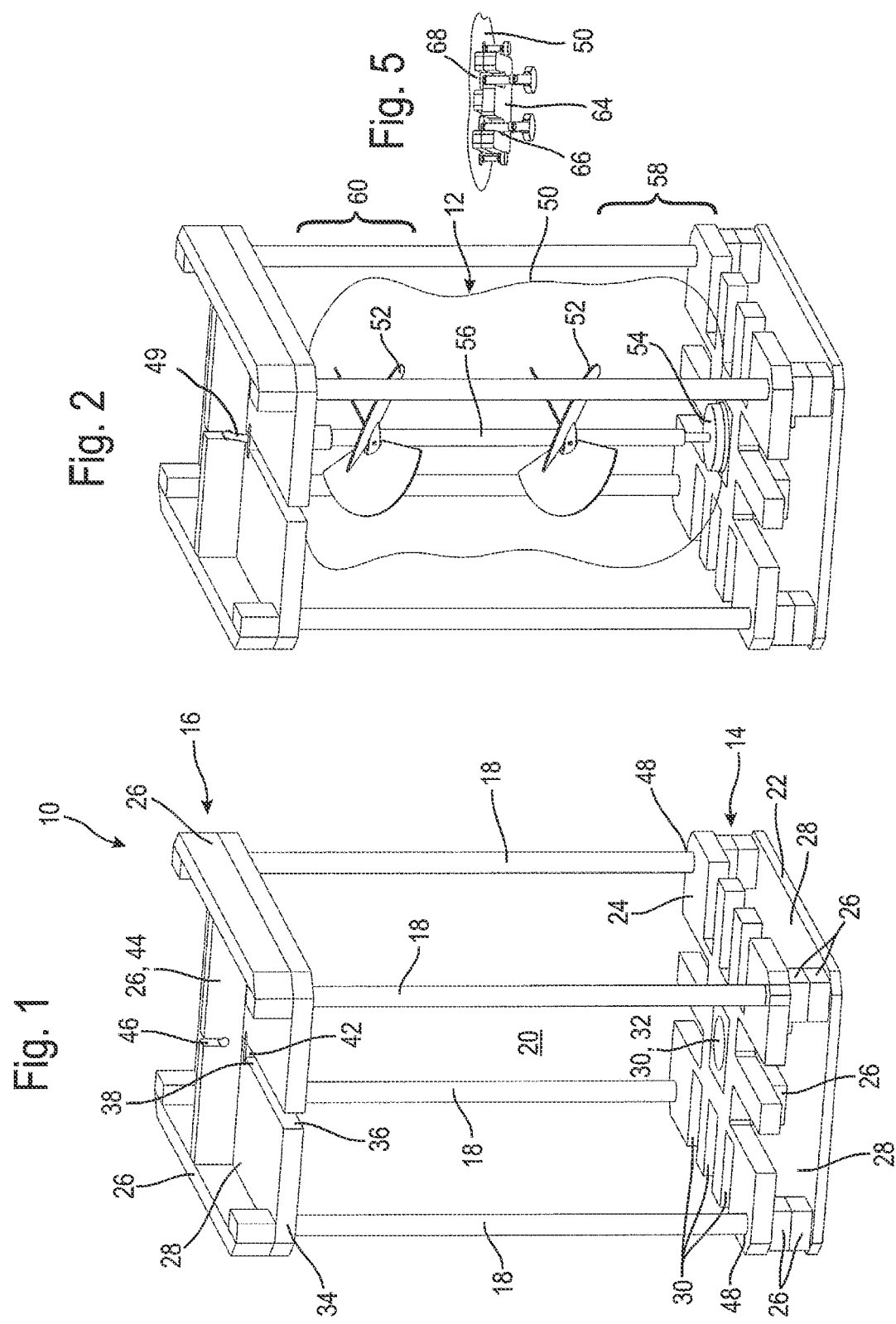

PROCESS FOR ASSEMBLING PACKAGING FOR A FLEXIBLE CONTAINER

FIELD OF THE INVENTION

This invention relates to a packaging for a flexible container, in particular for a disposable bag for use in a bioreactor. This invention furthermore relates to a transport unit with a flexible container which is received in such packaging.

BACKGROUND

In bioreactors certain microorganisms or plant or animal cells are cultivated under conditions as optimum as possible. There are often used pre-sterilized disposable bags which replace conventional culture vessels made of glass or stainless steel. The disposable bags already are equipped with a plurality of pre-mounted hoses. In addition, pre-sterilized stirring tools can be integrated into the bags, which via a magnetic body in the interior of the bag are coupled with the external stirrer motor of the bioreactor.

When transporting such disposable bags in ordinary packagings, it cannot be excluded that a damage of the bag can occur due to the contact of the bag with the stirring tools or other hard or sharp-edged parts of the hoses, such as hose clamps or other means for fixing the hoses in the roved-up condition. This is due to the fact that the bag based on its intended position of use usually is folded, packed and transported in the horizontal position.

U.S. Pat. No. 5,307,928 shows a transport packaging for household appliances which comprises an upper cover and a lower supporting device with a lower cover and four folded side elements in which the lateral edges of the appliance are accommodated. During the transport of the appliance the upper cover, the lower cover and the side elements are fixed at the appliance by straps, in order to ensure the protection of the appliance against transport damages.

From WO 2013/171340 A2 an exterior packaging for a bioreactor bag is known, which consists of a lid, a bottom and side walls. The exterior packaging includes a compartment for receiving the bioreactor bag, wherein the volume of the compartment is defined by a separating device with two gable walls running towards each other at an obtuse angle. The separating device is vertically shiftably arranged within the exterior packaging, so that the volume of the compartment can variably be adapted to different volumes of bioreactor bags.

SUMMARY

It is the object of the invention to provide a packaging which provides for safe transport and safe storage of a flexible container, in particular in consideration of the hoses which are mounted on the container and are to be stowed in the packaging.

This object is solved by a packaging with the claimed features. Advantageous and expedient aspects of the packaging according to the invention are indicated in the associated sub-claims.

The inventive packaging for a flexible container, in particular for a disposable bag for use in a bioreactor, comprises a bottom part for fixing a first portion of the container, a ceiling part for fixing an opposite second portion of the container, a receiving space which on a first side is defined by the bottom part and on an opposite second side is defined by the ceiling part, and struts arranged between the bottom part and the ceiling part, which fix a defined distance between the bottom part and the ceiling part.

The struts provided according to the invention serve as spacers between the bottom part and the ceiling part and hence define the height of the receiving space. With a knowledge of the dimensions of the container to be transported it thereby is possible to choose the distance between the bottom part and the ceiling part so large that in the transport condition the container fixed at these parts permanently is held in an unfolded condition, in which a pressure or frictional contact of the flexible container envelope with internal parts, such as a stirring tool, largely is excluded. In addition, the struts ensure that the packaging becomes a kind of frame in which the receiving space altogether has such a large volume that the flexible container envelope virtually always has a possibility for backing away from a contact with a hard or sharp-edged part. As compared to smooth side walls, as they are provided for example in the packaging according to WO 2013/171340 A2, the struts have the advantage that they are easier to grasp. This means that the packaging frame is easier to manipulate (carry, tilt, turn etc.) both during packaging and during unpacking. In the same advantageous way, the packaging according to the invention also can serve as packaging for storing the container before or after a transport.

The terms "bottom part" and "ceiling part" were chosen with regard to the preferred application of the invention, in which the orientations of the packaging and the flexible container play an important role, which will be discussed in more detail below. However, the terms are not to be understood in a limiting sense. In other applications, the bottom part need not necessarily be arranged at the bottom and the ceiling part need not necessarily be arranged at the top. For example, the two parts also can represent side parts.

The preferred material for the bottom part and/or the ceiling part is foamed material, not only because of the low density. From foamed material arbitrary shapes can be made, wherein the strength and compressibility are adaptable to the respective requirements.

According to a particularly preferred embodiment of the invention at least one compartment is formed in the bottom part and/or in the ceiling part, which is accessible from the receiving space via at least one passage opening. Such compartment serves for receiving one or more hoses which are connected to the container. For packaging, the respective hose is guided through the passage opening, so that most of the hose comes to lie in the compartment. Due to the spatial separation of the compartment from the receiving space, in which the container is accommodated, pressure or frictional contacts between container envelope and hose can be excluded. In addition, due to the specified guidance and placement of a hose in a separate compartment kinking of the hose can be avoided. This can be supported by further measures, such as rolling up and fixing of the hose portion present in the compartment. Compared to conventional packaging, unpacking of the container turns out to be easier, as each hose is found at a predetermined point. When several compartments are provided, in each of which only one hose is accommodated, entangling of the hoses thereby is prevented. It should be noted that the at least one compartment—apart from the at least one passage opening—need not be closed all around. Rather, the compartment should be accessible laterally, so that a hose can be placed therein or be removed therefrom more easily. In the case of several compartments, a compartment also can be connected with one or more adjacent compartments.

Preferably, the bottom part and/or the ceiling part includes a lower plate and an upper plate, which are separated from each other by one or more spacer elements, wherein the at least one compartment is defined by the plates and the spacer element(s). Due to the spaced arrangement of two plates one above the other a free space is obtained, in which the at least one compartment can be provided. The spacer elements at the same time serve as lateral boundaries of the compartment.

According to a particularly preferred embodiment of the invention the bottom part and/or the ceiling part has several passage openings which are each separately accessible from an outside of a plate of the bottom part and/or each separately from an outside of a plate of the ceiling part. The additional lateral accessibility of the passage openings provides for separately inserting the hoses into different passage openings and for stowing the same separately. A tangled mess of cables, more exactly a "mess of hoses" of several entangled hoses thereby is avoided, so that unpacking the container and putting the container with the hoses into operation can be carried out more comfortably.

The bottom part and/or the ceiling part with the compartment formed therein either can be formed in one piece or be composed of several parts and be designed as prefabricated assembly. In both cases packaging is simplified, as the bottom part and/or the ceiling part immediately is usable as a whole without preparatory work.

With regard to the preferred application of the packaging according to the invention a plate of the bottom part or of the ceiling part includes an oblong slot which extends from an outside of the plate to the inside. Into this slot a central discharge hose or other hose of a disposable bag to be packaged can be introduced laterally and be pulled to the center. The slot hence serves as passage opening for the hose, which then can be deposited on the side of the plate facing away from the receiving space. When the hose is rolled up and fixed on this side, so that the hose no longer can be pulled back into the receiving space, the slot merely serves as fixture for the bag.

According to a particular embodiment of the invention a spacer element includes a depression on the bottom part or ceiling part transversely to the longitudinal direction of the slot. The hose thus can be guided through the depression onto the side of the spacer element facing away from the slot and be deposited there, where it is safe from contacts with other parts of the container.

To prevent that, the hose again moves from the slot end to the outside, a recess extending across the slot can be formed in the plate before the inner slot end, into which recess a separate retaining part is insertable. The retaining element represents a barrier for the hose and ensures a defined, kink-free course of the hose.

For anchoring the struts, preferably both the bottom part and the ceiling part include opposite fixtures for the struts.

In turn with regard to the preferred application of the invention, a central receptacle in the bottom part or in the ceiling part is advantageous for a magnetic body of a mixing tool arranged in the container, which usually is arranged on an end portion of the container.

According to a development of the invention at least one separate fixture part for fixing one or more hoses, which extend from the flexible container, can be provided in the packaging. Such fixture parts ensure that there is no direct contact between hard or sharp-edged connectors, connecting pieces or other parts of the hoses and the flexible container. Undesired kinking of the hose portions which open into the container also is avoided by the fixation by means of the fixture parts. The fixture parts can flexibly be adapted to the respective hose designs in terms of shape, material etc., in order to ensure optimum protection against damages of the container and the hoses.

The fixture part for example can be designed such that at least one line receptacle in which at least one hose portion can be fixed is accessible via a passage. The hose portion thus can easily be introduced into the line receptacle and be clamped there and/or be held by friction.

The invention also creates a transport unit with a flexible container, in particular a bag for use in a bioreactor, wherein the container is received in a packaging as described above.

With respect to the advantages of this transport unit reference is made to the above explanations concerning the advantages of the packaging according to the invention.

According to the preferred application of the invention several hoses are mounted on an upper portion of the container with respect to the intended position of use of the container, which hoses are guided through one or more passage openings of the bottom part or the ceiling part into the compartment(s). In a disposable bag for use in a bioreactor, the required hoses already are mounted on corresponding connectors of the bag envelope and are delivered as unit. The majority of hoses opens into the upper portion of the bag, so that here especially it is required to stow the hoses orderly and safely.

Particularly preferably, the one or more passage openings of the bottom part and/or of the ceiling part each are accessible separately from an outside of a plate of the bottom part and/or each separately from an outside of a plate of the ceiling part. As explained already, the additional lateral accessibility of the passage openings provides for separately inserting the hoses into various passage openings and for separately stowing the same, whereby entangling of several hoses is avoided.

Preferably, each passage opening is connected with a separate compartment, so that a clear allocation of the passage openings to the compartments is ensured.

It is found to be advantageous to fix the container, with respect to its intended position of use, with an upper portion at the bottom part and with a lower portion at the ceiling part (upside down). As mentioned above, the majority of hoses is present at the upper portion of the container, just like e.g. a magnetic body for coupling the drive for the stirring tools. When the container then is packaged and transported upside down, the center of gravity of the container lies at the bottom and there is a much smaller risk of tilting of the transport unit.

When packaging a disposable bag, in which (only) one central hose is mounted on a lower portion, with respect to the intended position of use, it is advantageous to guide the same through a passage opening of the ceiling part in the form of a slot into the at least one compartment.

In a special embodiment a kink-free course of such hose is prevented in that the bottom part, or the ceiling part includes at least two support elements on which the hose is deposited.

According to a preferred embodiment the packaged container includes a shaft with a magnetic body of a mixing tool supported on an end of the shaft, which is inserted into a receptacle of the bottom part or the ceiling part. This receptacle offers additional protection against the magnetic body undesirably getting in contact with the container envelope.

In particular for a container which includes no shaft or other components that specify the height of the bag, it is expedient to adjust the arrangement and the lengths of the struts to the expansion of the received container in a first direction between the bottom part and the ceiling part such that in the directions vertical to the first direction the container does not or only slightly protrude between the struts. The less clearance the container has in these directions, the smaller is the risk of damage.

Further features and advantages of the invention can be taken from the following description and from the attached drawings to which reference is made.

BRIEF DESCRIPTION OF THE DRAWINGS

In the drawings:

FIG. 1 shows a perspective view of a packaging according to a first embodiment of the invention;

FIG. 2 shows a perspective view of the packaging of FIG. 1 with a disposable bag for a bioreactor as transport unit according to the invention;

FIG. 5 shows the fixture part of FIG. 4 with fixed hoses;

DETAILED DESCRIPTION

Figure 3:
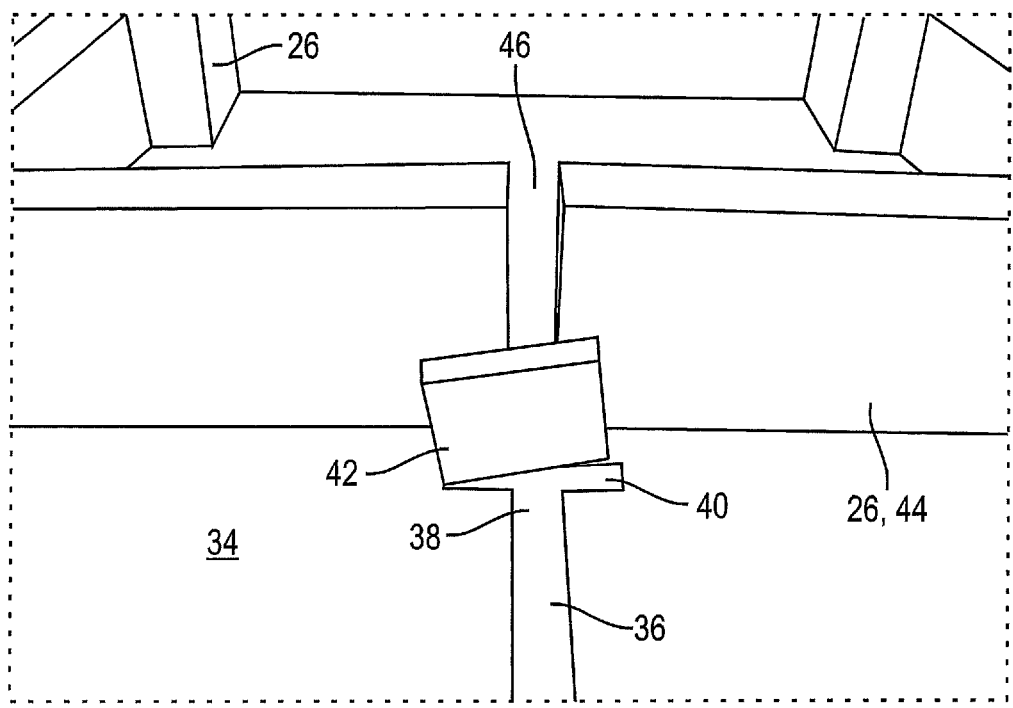
FIG. 3 shows a perspective detail view of the ceiling part of the packaging of FIG. 1.

FIGS. 1 and 2 show a first embodiment of a packaging 10 for a flexible container 12, more exactly a disposable bag (see FIG. 2), which is provided for use in a bioreactor. The packaging 10 comprises a bottom part 14, a ceiling part 16 and several column-like struts 18 which serve as spacers between the bottom part 14 and the ceiling part 16. The space defined by the bottom part 14, the ceiling part 16 and the struts 18 forms a receiving space 20 for the container 12 to be packaged.

For the sake of simplicity, the longitudinal direction of the struts 18 subsequently is referred to as vertical direction and the directions vertical thereto, in which the bottom part 14 and the ceiling part 16 extend, are referred to as horizontal directions, corresponding to the preferred use of the packaging 10, wherein these designations are not to be understood in a limiting sense.

The bottom part 14 substantially consists of a foamed material and includes a lower base plate 22 and an upper base plate 24, which are separated from each other by spacer elements 26. Between the lower base plate 22 and the upper base plate 24 a free space thus is located, which is divided into several compartments 28 by the spacer elements 26. A compartment 28 can laterally be closed completely or be connected with one or more adjacent compartments 28. At least some of the compartments 28 are accessible from outside in horizontal direction.

The upper base plate 24 has several vertical passage openings 30 through which the compartments 28 also are accessible in vertical direction. The passage openings 30 can have various shapes and dimensions depending on the requirement. In the illustrated exemplary embodiment the upper base plate 24 has several rectangular openings which are not closed on the outside, and a central receptacle 32.

The bottom part 14 can be formed in one piece or be composed of several individual parts. In the latter case, the individual parts are glued, braced, clamped, welded or otherwise connected to each other such that the bottom part 14 forms a prefabricated assembly and can be stored and moved as a whole.

Analogous to the bottom part 14, the ceiling part 16 is formed either in one piece or as prefabricated assembly and substantially consists of foamed material. On a ceiling plate 34 of the ceiling part 16 a plurality of spacer elements 26 are arranged on the side facing away from the bottom part 14, but no further plate for vertically delimiting the compartments indicated by the spacer elements. Such additional plate can, however, be provided optionally.

In the illustrated exemplary embodiment the ceiling plate 34 has an oblong slot 36 as vertical passage opening 30, which extends from an outside up to about the center of the ceiling plate 34. Shortly before the slightly enlarged central end 38 of the slot 36 a recess 40 extending transversely to the longitudinal direction of the slot 36 is formed in the ceiling plate 34, which can be filled by a separate retaining part 42 (see FIG. 3). On the opposite side of the slot end 38 an oblong spacer element 44 likewise extends transversely to the longitudinal direction of the slot 36. In the imaginary extension of the slot 36 this spacer element 44 includes a depression 46 on its free side facing away from the ceiling plate 34.

Particularly preferably, the bottom part 14, the ceiling part 16 and the struts 18 are fabricated of the same, gamma-sterilizable material, preferably polyethylene (PE). In principle, however, said parts also can be formed of another stable and fracture-proof material.

The bottom part 14 and the ceiling part 16 include opposite fixtures 48 for each strut 18. When the struts 18 are inserted into the fixtures 48 parallel to each other, a robust packaging frame is obtained, whose preferred use will be explained in more detail below.

Figure 4:
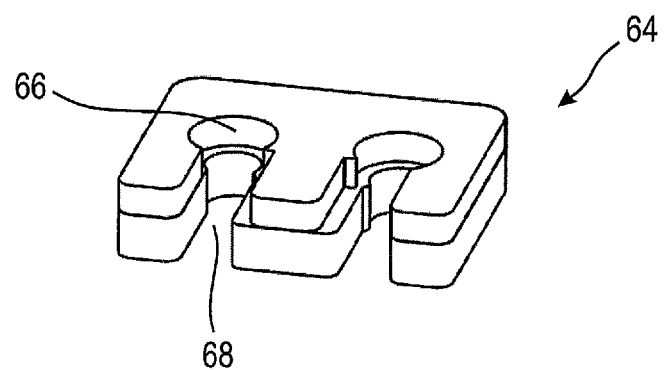
FIG. 4 shows a fixture part of a packaging according to the invention for fixing hoses with connectors.

Another optional part of the packaging 10 is the fixture part 64 shown in FIG. 4, of which several can be provided as well. The fixture part 64 is of comb-like shape and has several line receptacles 66 which are accessible via constricted passages 68.

The container 12 to be packaged here is a pre-sterilized disposable bag with a flexible envelope 50. The container 12 contains an integrated stirrer which includes several stirring tools 52 and a magnetic body 54. The stirring tools 52 and the magnetic body 54 are mounted on a central shaft 56. In addition, several fluid lines (hoses) (not shown in FIGS. 1 and 2) are connected to the container 12. According to the orientation in the condition of use as provided by the use of the container 12 in a bioreactor, the majority of these hoses are provided at the upper portion 58 of the container 12. To the lower portion 60 of the container 12 a central discharge hose 49 is connected (shown in FIG. 2). At least at some of the hoses connecting pieces, fixing clamps or other hard or sharp-edged elements are disposed.

For packaging, the container 12 initially is fixed with its upper end at the bottom part 14 of the packaging 10, wherein the magnetic body 54 arranged at the upper shaft end is inserted into the central receptacle 32 of the upper base plate 24. The hoses mounted at the upper portion 58 of the container 12 are guided through the respectively nearest passage opening 30 and received in the compartment 28 underneath. The hose portions present in the compartments 28 can be fixed in the rolled-up condition e.g. by clamps and/or be protected by wrapping or bagging.

Subsequently, the struts 18 are inserted into the fixtures 48 of the bottom part 14, and the container 12 is pulled upwards at the central discharge hose 49. For fixing the lower container portion 60 at the ceiling part 16, the discharge hose 49 is pulled to the center through the slot 36 in the ceiling plate 34 and guided over the depression 46 in the spacer element 44, so that the remaining part of the discharge hose 49 comes to lie on the ceiling plate 34 on the side facing away from the slot 36. This hose part, too, can be fixed in the rolled-up condition and be protected by further measures.

To ensure that the discharge hose 49 takes a defined, kink-free course from the receiving space 20 via the spacer element 44, the retaining part 42 is inserted into the recess 40 after the discharge hose 49 has been pulled up to the slot end 38. The retaining part 42 prevents that the discharge hose 49 can be shifted to the outside. (When unpacking the container 12 later on, the retaining part 42 is again removed from the recess 40).

Before, during or after fixing the lower container portion 60 at the ceiling part 16, the ceiling part 16 is put onto the struts 18.

According to the preferred transport condition as shown in FIG. 2, the container 12 now is upside down with respect to its future condition of use, i.e. accommodated in the packaging 10 with its upper portion 58 at the bottom and its lower portion 60 at the top.

The distance between the bottom part 14 and the ceiling part 16 as defined by the length of the struts 18 is chosen such that no or only a negligible part of the fixed container 12 can protrude laterally from the packaging frame between the struts 18.

At an arbitrary time before the container finally is made ready for transport, the separate fixture parts 64 still can be inserted, as shown in FIG. 5. The fixture parts 64 serve to fix hoses extending from the flexible envelope 50 of the container 12. For this purpose, the hoses are pressed through the passages 68 into the line receptacles 66 of the fixture parts 64 close to the envelope 50. It thereby is achieved that those portions of the hoses which open into the container 12 are fixed such that they more or less vertically extend from the envelope 50 to the outside. This fixation ensures that hard or sharp-edged connectors, connecting pieces or other parts of the hoses are kept away from the flexible envelope 50, in order to prevent damages at the envelope 50 itself, but also at the hoses and their connectors, connecting pieces etc.

To finally make the container 12 ready for transport, the packaging frame also is covered with one or two plastic sacks or the like, which are welded closed or closed with adhesive tape, before the entire unit then is put into a shipping carton and secured with strapping tapes or packing tape.

The packaging 10 as shown in FIGS. 1 to 5 is suitable for large flexible containers 12 with a filling volume in the order of magnitude of 500 liters, 1,000 liters, 2,000 liters or more.

Figure 7:
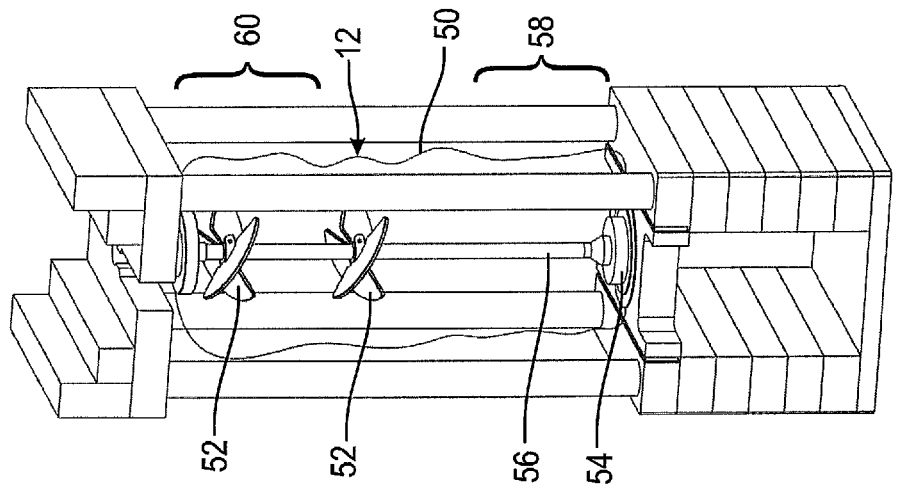
FIG. 7 shows a perspective view of the packaging of FIG. 6 with a disposable bag for a bioreactor as transport unit according to the invention.
Figure 6:
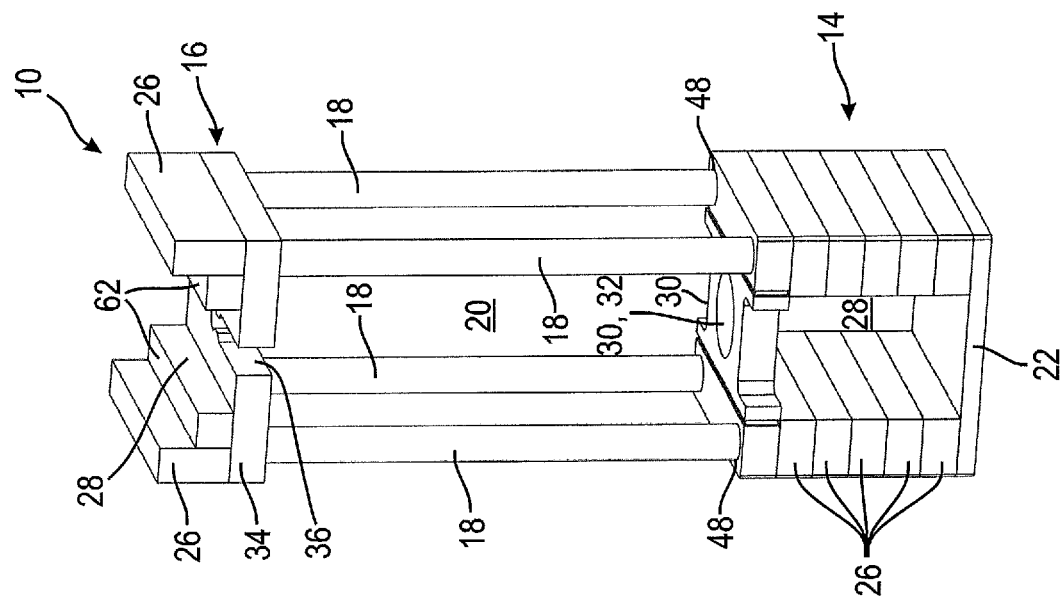
FIG. 6 shows a perspective view of a packaging according to a second embodiment of the invention.

FIGS. 6 and 7 show a second embodiment of the packaging 10, which is suitable for smaller containers 12 with a filling volume in the order of magnitude of 50 liters or 200 liters. The second embodiment substantially has the same construction as the first embodiment and only differs in the dimensions of the individual elements and in the concrete design of the bottom part 14 and the ceiling part 16. In the second embodiment only a single compartment 28 is formed in the bottom part, which however has a larger vertical height as compared to the first embodiment. A spacer element extending across the ceiling plate 34 and a separate retaining element are not provided in the ceiling part 16.

The ceiling part 16 instead includes two support elements 62 which are lower than the outer spacer elements 26 of the ceiling part 16. The rolled up discharge hose 49 comes to lie on these support elements 62. Thus, the support elements 62 here ensure that kinking of the discharge hose 49 is avoided.

Both embodiments have in common that the bottom parts 14 and the ceiling parts 16 each have a rectangular, particularly preferably a square basic shape. This shape, however, is not absolutely necessary, just like the number of struts 18, i.e. depending on the requirement there can also be provided less (in particular three) or more than four struts 18, wherein an arrangement outdoors always is preferred. The bottom part 14 and/or the ceiling part 16 also can include several intermediate trays with passage openings 30, so that the compartments 28 for the hoses etc. also can be arranged one above the other.

Of course, one or more fixture parts 64 can also be provided in the second embodiment.

In principle, features of the various embodiments can be combined with each other in a suitable way, in order to obtain further embodiments in accordance with the invention.

The described embodiments each relate to a packaging 10 for a special disposable bag which is provided for use in a bioreactor. The invention is, however, not limited to this application. Rather, the packaging 10 according to the invention also can be used for other flexible containers or similar objects.

LIST OF REFERENCE NUMERALS 10 packaging
12 container
14 bottom part
16 ceiling part
18 strut
20 receiving space
22 lower base plate
24 upper base plate
26 spacer element
28 compartment
30 passage opening
32 receptacle
34 ceiling plate
36 slot
38 slot end
40 recess
42 retaining part
44 spacer element
46 depression
48 fixture
50 envelope
52 stirring tool
54 magnetic body
56 shaft
58 upper container portion
60 lower container portion
62 support element
64 fixture part
66 line receptacle
68 passage

The invention claimed is:

1. A process for assembling packaging for a flexible container,
wherein the flexible container comprises an upper portion and an opposite lower portion, and the packaging comprises a bottom part with fixtures for receiving struts, a ceiling part with fixtures for receiving struts, struts arranged between the bottom part and the ceiling part, and a receiving space defined on one side by the bottom part and by the ceiling part on an opposing side, the process comprising:

fixing the upper portion of the flexible container to the bottom part of the packaging, then inserting the struts, parallel to each other, into the fixtures of the bottom part of the packaging, followed by steps wherein the lower portion of the flexible container is fixed to the ceiling part of the packaging either before, during or after the ceiling part of the packing packaging is placed onto the struts so that the struts are inserted into the fixtures of the ceiling part of the packaging, wherein the flexible container comprises a stirrer comprising a magnetic body mounted on a shaft, wherein the upper portion of the flexible container is fixed at the bottom part of the packaging by a process that includes arranging the magnetic body at an upper end of the shaft and inserting the magnetic body into a central receptacle of the bottom part of the packaging.

2. The process according to claim 1, wherein the flexible container comprises a discharge hose at the lower portion of the flexible container wherein, after the struts are inserted into the fixtures of the bottom part of the packaging, the bottom part of the flexible container is fixed to the ceiling part of the packaging by a process that includes pulling the discharge hose at the lower portion of the flexible container through a slot in the ceiling part of the packaging.

3. The process according to claim 2, wherein the flexible container is a bioreactor bag.

4. A process for assembling packaging for a flexible container, wherein the flexible container comprises an upper portion and an opposite lower portion, and the packaging comprises a bottom part with fixtures for receiving struts, a ceiling part with fixtures for receiving struts, struts arranged between the bottom part and the ceiling part, and a receiving space defined on one side by the bottom part and by the ceiling part on an opposing side, the process comprising:

fixing the upper portion of the flexible container to the bottom part of the packaging, then inserting the struts, parallel to each other, into the fixtures of the bottom part of the packaging, followed by steps wherein the lower portion of the flexible container is fixed to the ceiling part of the packaging either before, during or after the ceiling part of the packaging is placed onto the struts so that the struts are inserted into the fixtures of the ceiling part of the packaging, wherein the flexible container comprises a discharge hose at the lower portion of the flexible container wherein, after the struts are inserted into the fixtures of the bottom part of the packaging, the bottom part of the flexible container is fixed to the ceiling part of the packaging by a process that includes pulling the discharge hose at the lower portion of the flexible container through a slot in the ceiling part of the packaging.

* * * * *